United States Patent [19]

Brown et al.

[11] Patent Number: 4,732,850
[45] Date of Patent: Mar. 22, 1988

[54] FRANGIBLE CONTAINER WITH RUPTURING DEVICE

[75] Inventors: James R. Brown, Colonia, N.J.; Steven T. Buglino, Bayport, N.Y.

[73] Assignee: E. R. Squibb & Sons, Inc., Princeton, N.J.

[21] Appl. No.: 752,283

[22] Filed: Jul. 5, 1985

[51] Int. Cl.[4] ............................ C12Q 1/22; C12M 1/24
[52] U.S. Cl. ...................................... 435/31; 435/296; 435/810; 206/219; 206/569
[58] Field of Search ................. 435/31, 292, 293, 294, 435/296, 299, 300, 810; 206/219, 528, 532, 534, 569; 215/DIG. 8; 422/102

[56] References Cited

U.S. PATENT DOCUMENTS

| | | |
|---|---|---|
| 1,332,985 | 3/1920 | Jarrett ................................ 206/219 |
| 2,487,236 | 11/1949 | Greenberg . |
| 3,297,184 | 1/1967 | Andelin ............................ 435/296 X |
| 3,440,144 | 4/1969 | Andersen . |
| 3,616,263 | 10/1971 | Anandam ......................... 435/296 X |
| 3,661,717 | 5/1972 | Nelson . |
| 3,907,106 | 9/1975 | Purrmann et al. ................. 206/219 |
| 4,136,775 | 1/1979 | Zaltsman . |
| 4,252,904 | 2/1981 | Nelson et al. . |
| 4,291,122 | 9/1981 | Orelski . |
| 4,304,869 | 12/1981 | Dyke . |
| 4,416,984 | 11/1983 | Wheeler, Jr. . |
| 4,461,837 | 7/1984 | Karle et al. . |
| 4,528,268 | 7/1985 | Andersen et al. ..................... 435/31 |
| 4,579,823 | 4/1986 | Ryder ............................. 435/31 X |

FOREIGN PATENT DOCUMENTS 0152298 8/1985 European Pat. Off. ............. 435/31

*Primary Examiner*—Robert J. Warden
*Assistant Examiner*—Randall E. Deck
*Attorney, Agent, or Firm*—L. S. Levinson; S. J. Asman

[57] ABSTRACT

A biological indicator is made of a vial which contains a "spore dot", a nutrient solution in a frangible ampoule, and means for positioning the spore dot and for breaking the ampoule to release the nutrient solution when the cap of the vial is fully pressed on. The nutrient solution typically contains a pH indicator to determine whether all active spores on the strip were killed by a sterilization process which takes place prior to breaking the ampoule.

8 Claims, 5 Drawing Figures

FRANGIBLE CONTAINER WITH RUPTURING DEVICE

BACKGROUND OF THE INVENTION

The present invention relates to an apparatus for rupturing a sealed, frangible container, such as a glass ampoule of the type used in a biological tester.

Hermetically sealed glass ampoules are widely used, particularly in the health care industry, to hold fluids that must be protected against contamination until they are ready for use. In particular, such ampoules are often used in biological indicating systems in which it is desirable to provide immediate and massive contact of a fluid contained in an ampoule with an external item. In one commonly used method of testing sterilizers, for example, a piece of filter paper having standardized biological spores of a strain sufficiently resistant to the sterilization medium are placed on a carrier (such as a piece of filter paper called a "spore strip" or "spore dot") which is exposed to the sterilization process being tested. Then the "sterilized" strip is exposed to a large amount of fluid nutrient. Sterilization of the standardized spore strain insures sterilization of bacterial strains in the chamber load, while survival of the standardized spore strain indicates unsatisfactory sterilization of the load.

Survival of the spores subsequent to the sterilization process is typically determined by mixing a test solution consisting of a nutrient growth medium containing a pH indicator with the spores and incubating the culture for growth. In spore fermentation, for example, glucose contained in the growth medium is utilized by viable spores, and pyruvic acid is produced as a by-product. Pyruvic acid lowers the pH of the test solution, thereby causing the pH indicator in the solution to change color. If there are no viable spores following sterilization, the pH (and thus the color) of the test solution remains essentially unchanged.

The immediate and massive outflow of the nutrient containing fluid from the ampoule to conduct the procedure described above has been described heretofore in U.S. Pat. Nos. 3,440,144, 3,661,717, and 4,304,869. While the methods and apparatus described therein are effective to provide the desired immediate outflow of the contents of the ampoule, some of the techniques described therein pose the risk of injury to the operator as well as the possibility of contamination. Also, those methods do not provide a simple apparatus for effectively mixing the nutrient fluid.

SUMMARY OF THE INVENTION

The present invention overcomes the disadvantages inherent in conventional apparatus used to rupture a sealed, frangible container, such as an ampoule. The present invention uses a substantially rigid tubular vial, in which the frangible ampoule is retained. The ampoule coacts with a spore dot positioning device which serves both to retain the spore dot in a consistent location in the vial and to act as a means for engaging the ampoule. The positioning device provides sufficient lateral pressure on the side of the ampoule to rupture it. The action between the positioning device and the ampoule may be provided in a variety of ways, but preferably is provided by using a positioning device which encircles the ampoule at a position near the top of the ampoule. As the top of the vial is depressed, the ampoule is centered within the vial and the spore dot positioning device exerts a lateral force on the side of the ampoule, thereby rupturing it. In addition, a glass bead may be used at the bottom of the vial as a means for holding the bottom of the ampoule in an off center position to assist in applying sufficient pressure on the side of the ampoule to cause it to fracture. If the glass bead is used, it also serves to create a reservoir for the collection of moisture and condensate at the bottom of the vial, thereby helping to prevent such moisture from acting as a barrier to steam penetration. Accordingly, when force is applied, typically by pressing the cap of the vial on tighter, the lateral pressure on the side of the ampoule increases until the ampoule fractures.

The present invention thereby provides an apparatus for rupturing a sealed, frangible container which comprises a substantially rigid tubular vial defining a closed interior chamber for receiving both the ampoule and the spore dot positioning means disposed within the tubular vial for engaging a very small area of the frangible container with sufficient pressure to rupture it. In addition, the spore dot positioning means also serves as a means for holding the spore dot in a consistent position when the vial is used in a sterilization procedure.

DETAILED DESCRIPTION OF THE PREFERRED EMBODIMENT

Figure 1:
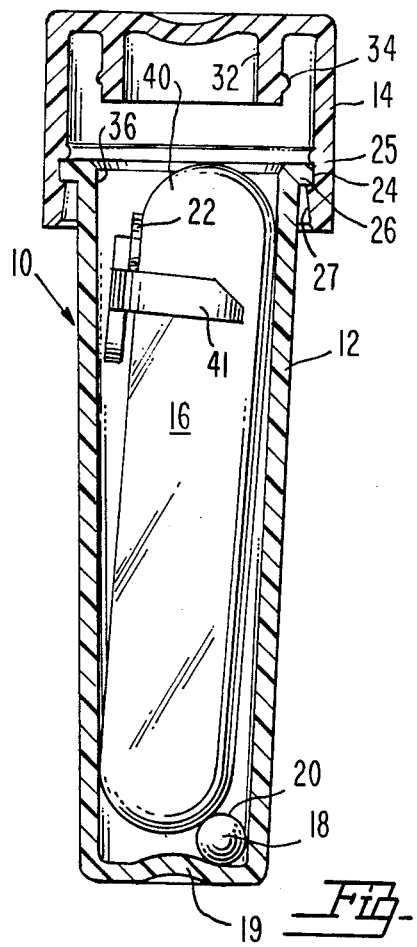
FIG. 1 illustrates a cross-sectional view of the preferred embodiment of the present invention in the pre-ruptured position.

Referring now to FIG. 1, the present invention 10 is comprised of a substantially rigid tubular vial 12 having a press-on cap 14. Both the vial 12 and the cap 14 are made of material which is impermeable to gas flow. In the preferred embodiment of the invention 10, the vial 12 is made of polycarbonate, and the cap 14 is made of polypropylene. While other materials may be used, the selected materials must be able to withstand sterilization at about 273° F. In addition, the material which the vial 12 is made of should preferably be clear and relatively non-deformable.

The tubular vial 12 holds a frangible container, such as ampoule 16, which contains a nutrient solution. Within the vial 12 of the preferred embodiment of the invention 10, there may be a non-compressible insertable means. In the preferred embodiment of the invention 10, a non-compressible insertable means comprised of a glass bead 18 is used. The main function of the glass bead 18 is to help to hold the lower portion of the ampoule 16 off center within the vial 12. In addition, the glass bead 18 also acts, together with the bottom of the ampoule 16, to create a reservoir at the bottom of the vial 12 where excess moisture and steam condensate can collect, rather than allowing such condensate to act as a physical barrier to steam penetration. Accordingly, as will be obvious to those of ordinary skill in the art, the glass bead 18 may be omitted or replaced by another non-compressible object capable of providing a similar function.

Figure 5:
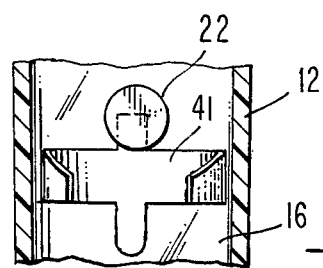
FIG. 5 is an exploded side view of the spore dot and the positioning means.

A "spore dot" or spore containing test strip 22, is held in place by a spore dot positioning device 41 which fits around the ampoule 16 adjacent the top of the ampoule 16 (see FIG. 5). The positioning device 41 acts as a fulcrum and imparts lateral pressure on the upper portion of the ampoule 16 when downward pressure is applied to the cap 14, tending to center the ampoule 16 within the vial 12. Maintaining the spore dot 22 in a uniform position is important in terms of maintaining uniform performance under controlled sterilization conditions. However, the major advantage of the positioning device 41 is that it acts as a means for elevating the spore dot 22 to a position where it is exposed to sterilization conditions more closely representative of those in the sterilization chamber and the load being monitored, while permitting subsequent combination of the growth medium and the spore dot 22.

The positioning device 41 substantially overcomes two known disadvantages of other biological indicators. In particular, in gravity (downward air displacement) type steam sterilization cycles, the air is often entrapped in closed end tubular vials, especially if they are oriented with their cap end up. Such entrapped air greatly retards steam penetration to the bottom of the vial, resulting in a lag in kill time not representative of the actual conditions in the chamber or load. This can result in survival of resistant spores and rejection of processed loads that are actually sterile. A gradient of air, air and steam, and steam is formed in the vial 12 from the bottom to the top. Thus, the closer the spore dot 22 is positioned to the top of the vial 12, the more representative the exposure conditions, relative to the chamber and load, will be.

In pre-vacuum, high temperature (270° F.) steam sterilization cycles, the air entrapment problem is not ususally present, since a pre-vacuum phase removes the air from the chamber and load prior to steam injection. However, a different, even more significant, problem exists. Due to the closed end nature of the vial 12, especially in the vertical (cap up) position, a significant amount of condensate can form and collect in the vial 12. The amount of condensate formed is directly proportional to the mass and initial temperature of the the mass, since steam condenses on the mass until its temperature is equivalent to that characteristic of the pressure of steam in the chamber. If the spore dot 22 is near the bottom of the vial 12 or in contact with condensate at or near the middle of the vial, destruction of resistant spores will be retarded due to the physical barrier which the condensate forms. Elevation of the spore dot 22, by the positioning device 41, prevents this from occurring.

Figure 3:
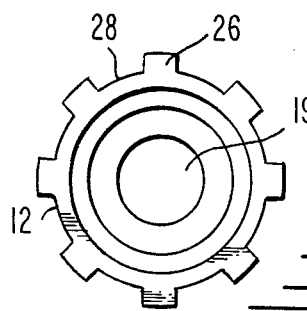
FIG. 3 is a top view of the vial showing the spore dot positioning means.
Figure 4:
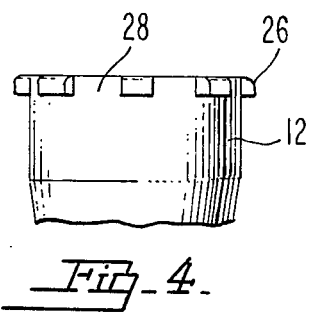
FIG. 4 is a side view of the top of the vial.

The cap 14 includes a detent 24 designed to coact with an interrupted ring shoulder 26 at the top of the vial 12, which keeps the cap 14 on the vial 12 (See FIGS. 1, 3, and 4).

Figure 2:
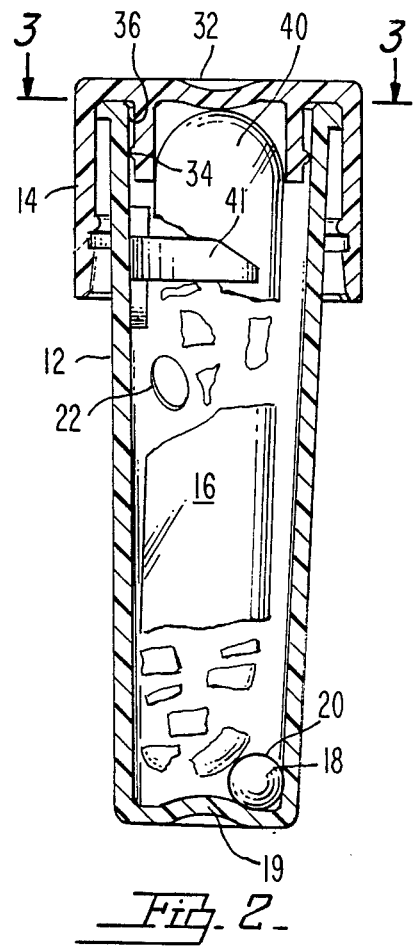
FIG. 2 is a cross-sectional view illustrating the preferred embodiment of the invention in a ruptured position.

A cam surface 25 on the top of the interrupted ring shoulder 26 acts with a cam surface 27 on the cap 14 to assist in assembling the cap 14 on the vial 12. The sterilizing atmosphere, whether steam or a gas, such as ethylene oxide, is able to enter the vial 12 when the cap 14 is in the loosened position shown in FIG. 1, by following a route through interruptions 28, in the interrupted ring shoulder 26 (See FIGS. 3 and 4) which allows gas to pass between the vial 12 and the cap 14, respectively. In addition, the cap 14 preferably includes a recessed portion 32 having a sealing ring 34 formed thereon. Accordingly, when the cap 14 is fully seated, as shown in FIG. 2, the sealing ring 34 bears against the inner wall 36 of the vial 12, thereby providing an air tight seal when the cap 14 is depressed.

As shown, the recess 32 is configured to receive the top portion 40 of the ampoule 16. Accordingly, when the cap 14 is tightened by pressing it onto the vial 12, as shown in FIG. 2, the inner recess 32 of the cap 14 acting as a centering device, engages the top 40 of the ampoule 16 imparting lateral movement of the ampoule 16 towards the center of the vial 12. As the ampoule 16 moves toward the center of the vial 12, the spore dot positioning device 41, acting as a fulcrum, limits the lateral movement of the ampoule 16 towards the center of the vial 12, and pressure is applied between the ampoule 16, the spore dot positioning device 41 and the vial wall 12.

An additional non-compressible insertable means may be included in the vial 12. In the preferred embodiment of the invention 10, the non-compressible insertable means is comprised of a glass bead 18. However, as will be obvious to those of ordinary skill in the art, the glass bead 18 may be omitted or replaced by another non-compressible object capable of performing the same function. In the preferred embodiment of the invention 10, there is a raised area 19 on the bottom of the tubular vial 12 which is also preferably constructed of a non-compressible material. The glass bead 18 acts to keep the ampoule 16 off-center in relation to the vial 12 and the cap 14. As additional downward pressure is applied to the cap 14, it is transferred to and through the ampoule 16 to the glass bead 18, imparting the downward pressure of the ampoule 16 on the glass bead 18 at the point of tangency 20. Accordingly, if present the glass bead 18 may assist in fracturing the ampoule 16 at the point of tangency 20 between the glass bead 18 and the ampoule 12.

As more downward pressure is applied to the cap 14, the interaction of the various movement and pressures causes the ampoule 16 to rupture, releasing the nutrient solution contained in the ampoule 16. The spore dot 22, held against the ampoule wall 16 by the positioning device 41 is also released when the ampoule 16 ruptures, and the spore dot 22 is then pushed by or falls from the positioning device 41 into the nutrient solution released from the ampoule 16.

In order to use the apparatus of the present invention, a test pack is made up. The test pack comprises the biological indicator 10 of the present invention in the middle of a pack which may contain towels, surgical gowns, lab sponges, or equivalent linens, or other medical supplies or devices. The test pack is passed through the sterilizer with the cap 14 in the loosened position shown in FIG. 1. Thereafter, the biological indicator 10 is removed from the test pack, and the ampoule 16 is fractured, in the manner described above, in order to release nutrients from the ampoule 16 onto the spore dot 22. Closing the cap 14 to fracture the ampoule 16 also serves to seal the vial 12 preventing the escape of nutrient solution either by leakage or by evaporation.

Following the release of the nutrient solution to saturate the spore dot 22, the biological indicator 10 is placed into an incubator which is set at a temperature which encourages spore growth. Following an appropriate incubation period, typically about 48 hours, the color of the nutrient solution is checked. If active spores are growning, the pH of the nutrient solution will decrease, causing the pH indicator in the nutrient solution to change color, as is well known in the art.

A particular advantage of the present invention 10 is that the positioning device 41 serves to hold the spore dot 22 in a uniform position, when compared to the devices heretofore known. Accordingly, the results are more consistent than those provided by the devices of the prior art.

I claim:

1. A frangible container and rupturing device comprising:
   (a) a substantially non-deformable tubular vial;
   (b) a sealed, frangible container within said tubular vial, said tubular vial having a cap which presses onto said sealed, frangible container, said cap including means for centering the top of said container within said vial; and
   (c) fulcrum means attached to said container near the end of said container adjacent to said cap of said vial, whereby when said cap is depressed said means for centering said container engages said container and causes said fulcrum means to provide a lateral force against the side of said container thereby providing sufficient pressure to rupture said container when said cap fully engages said vial.

2. The frangible container and rupturing device of claim 1 wherein said cap includes a detent and said vial includes an interrupted shoulder ring for receiving and detent, whereby said cap is retained on said vial when said cap is not fully pressed onto said vial.

3. The frangible container and rupturing device of claim 2 further comprising a non-compressible means at the bottom of said vial which serves to hold the bottom of said container in an off center position within said vial while also serving to create a reservoir within said vial wherein moisture and condensate can be retained.

4. The frangible container and rupturing device of claim 3 wherein said non-compressible means contained within said vial comprises a glass bead.

5. The frangible container and rupturing device of claim 4 wherein the bottom of said vial includes a raised area which serves to position said glass bead between said vial and said container.

6. A biological indicator comprising the frangible container and rupturing device of claim 1 and further comprising:
   (a) a spore containing test strip which is held by said fulcrum means; and
   (b) a solution within said frangible container, whereby the fracture of said frangible container results in said solution being dispersed on said test strip.

7. The biological indicator of claim 6 wherein said solution is a nutrient solution.

8. The biological indicator of claim 7 wherein said nutrient solution contains a pH indicator.

* * * * *

UNITED STATES PATENT AND TRADEMARK OFFICE
CERTIFICATE OF CORRECTION

PATENT NO. : 4,732,850

DATED : March 22, 1988

INVENTOR(S) : Brown et al.

It is certified that error appears in the above—identified patent and that said Letters Patent is hereby corrected as shown below:

Title page, field [73], replace the Assignee "E. R. Squibb & Sons, Inc." with -- Surgicot, Inc. --.

Column 5, line 29, delete "and" substitute therefore -- said --.

Signed and Sealed this

Eighth Day of November, 1988

Attest:

DONALD J. QUIGG

Attesting Officer

Commissioner of Patents and Trademarks